United States Patent [19]

Ritter et al.

[11] Patent Number: 5,159,106
[45] Date of Patent: Oct. 27, 1992

[54] PROCESS FOR THE IMPROVED PRODUCTION OF (METH)ACRYLIC ACID ESTERS OF POLYHYDRIC ALCOHOLS (VI)

[75] Inventors: Wolfgang Ritter, Haan; Hans-Dieter Sitz, Rommerskirchen; Ludwig Speitkamp, Duesseldorf, all of Fed. Rep. of Germany

[73] Assignee: Henkel Kommanditgesellschaft auf Aktien, Duesseldorf-Holthausen, Fed. Rep. of Germany

[21] Appl. No.: 679,073
[22] PCT Filed: Dec. 15, 1989
[86] PCT No.: PCT/EP89/01546
§ 371 Date: Aug. 20, 1991
§ 102(e) Date: Aug. 20, 1991
[87] PCT Pub. No.: WO90/07483
PCT Pub. Date: Jul. 12, 1990

[30] Foreign Application Priority Data

Dec. 24, 1988 [DE] Fed. Rep. of Germany ....... 3843843

[51] Int. Cl.$^5$ .............................................. C07C 69/52
[52] U.S. Cl. .................................................... 560/224
[58] Field of Search ......................................... 560/224

[56] References Cited

U.S. PATENT DOCUMENTS

| 3,896,161 | 7/1975 | Borden | 560/224 |
| 4,511,732 | 4/1985 | Hicks | 560/224 |
| 4,512,910 | 4/1985 | Schmidle | 560/224 |
| 4,859,792 | 8/1989 | Powanda et al. | 560/224 |

FOREIGN PATENT DOCUMENTS 1165349 7/1986 Japan .

*Primary Examiner*—Paul J. Killos
*Attorney, Agent, or Firm*—Ernest G. Szoke; Wayne C. Jaeschke; Henry E. Millson, Jr.

[57] ABSTRACT

A process for the production of (meth)acrylic acid esters of polyhydric alcohols by reaction of the reactants in the presence of acidic esterification catalysts with addition of polymerization inhibitors to the reaction mixture and purging of the reactor interior with an oxygen-containing gas stream. The process is characterized in that that part of the reactor interior filled with gas phase is charged with finely divided liquid droplets containing polymerization inhibitor.

26 Claims, No Drawings

PROCESS FOR THE IMPROVED PRODUCTION OF (METH)ACRYLIC ACID ESTERS OF POLYHYDRIC ALCOHOLS (VI)

This invention relates to a process for the production of esters of acrylic acid and/or methacrylic acid—hereinafter referred to as (meth)acrylic acid esters—with polyhydric alcohols by reactino of the reactants in the presence of acidic esterification catalysts with addition of polymerization inhibitors to the reaction mixture. The process according to the invention operates in particular with the additional measure of purging the reaction zone with an oxygen-containing gas stream to improve the inhibitor effect and to promote the discharge from the reaction zone of the water accumulating as condensation product from the esterification reaction.

(Meth)acrylic acid esters of polyhydric alcohols, particularly from the group of dihydric to tetrahydric aliphatic saturated alcohols and their alkoxylation products, are being used to an increasing extent as highly reactive constituents in radiation-curing systems. Polyfunctional (meth)acrylic acid esters of the type in question may be used, for example, as paint constituents for hardening by electron beams or as a constituent of UV-hardening printing inks or corresponding paints, surfacing, molding or encapsulating compounds or even in adhesives, particularly anaerobic adhesives. However, their production is not without problems. The end products are required in particular to be colorless with a low acid value, high stability in storage and hardly any odor. (Meth)acrylic acid esters of the type in question generally cannot be purified by distillation on account of their high molecular weight and their high reactivity. Accordingly, the products are intended to accumulate directly as colorless products of the esterification reaction. The esterification reaction requires the presence of highly effective inhibitors which, in turn, should not initiate any unwanted secondary reactions, for example in the form of discoloration. In addition, it may be desirable not only to protect the liquid reaction product against unwanted polymerization reactions during the esterification, but also to ensure adequate inhibition of the entire reaction zone including both the inner gas space and also the wall surfaces in contact with the inner gas space. This counteracts the danger of unwanted polymer formation, for example, on such unprotected wall surfaces, the washing off of such polymers into the reaction product in turn leading to an unwanted increase in viscosity in the end product or to unwanted insoluble particles.

Extensive literature is available on the product of such polyfunctional (meth)acrylic acid esters of polyhydric alcohols, cf. in particular DE-OS 29 13 218 and the relevant literature cited therein. Thus, it is known from DE-AS 12 67 547 and from the Journal "Chem. and Ind." 18 (1970), 597, that polyfunctional (meth)acrylic acid esters can be produced by azeotropic esterification of (meth)acrylic acid with polyhydric alcohols in the presence of acidic catalysts and polymerization inhibitors, such as phenols, phenol derivatives, copper, copper compounds or phenothiazine. Organic or inorganic acids or acidic ion exchangers are used as the acidic catalysts, p-toluene sulfonic acid and sulfuric acid being preferred. The esterification reaction takes place under azeotropic conditions using entraining agents for removal of the water of reaction, for example at temperatures in the range from 40° to 120° C. Suitable entraining agents are, for example, aliphatic or cycloaliphatic or aromatic hydrocarbons or mixtures thereof having boiling ranges within the stated temperature limits.

It is proposed in DE-OS 29 13 218 cited above to carry out the azeotropic esterification in the presence of at least one organic ester of phosphorous acid in addition to a phenol-based inhibitor in order to improve the esterification reaction and to obtain (meth)acrylic acid esters of the type mentioned which are not purified by distillation. This phosphiate-based inhibitor is intended to be added in particularly by means of a carrier gas and is apparently used above all to promote inhibition of the inner reaction zone filled with gas or vapor phase and to reduce color intensity. Thus, it is also proposed in particular to remove residual solvent, residues of reactive constituents and volatile secondary products from the esterification product after the azeotropic esterification reaction by blowing in air or nitrogen, this gas phase being said to be enriched or saturated with organic phosphites.

The problem addressed by the present invention is not only effectively to stabilize the reactive liquid phase by polymerization inhibitors, but also to protect the entire interior of the reactor against unwanted polymerization reactions. However, the invention seeks in this regard to eliminate the need for gaseous complex inhibitor systems. More particularly, the problem addressed by the invention is to enable the same inhibitor to be used both for protecitng the reactive liquid phase and also for protecting the gas- or vapor-filled interior and those solid surfaces in contact with these parts of the reactor interior. Another problem addressed by the invention is to enable the application inhibitor required in practice for the highly reactive systems in question here to be simultaneously used as a reaction inhibitor in the synthesis of the polyfunctional (meth)acrylic acid esters. The problems addressed by the invention are solved by the new process technology described hereinafter.

Accordingly, the present invention relates to a process for the production of (meth)acrylic acid esters of polyhydric alcohols by reaction of the reactants in the presence of acidic esterification catalysts with addition of polymerization inhibitors to the reaction mixture and purging of the reaction zone with an oxygen-containing gas stream, characterized in that that part of the reactor interior which is filled with gas phase is charged with fine liquid droplets containing polymerization inhibitor.

In the preferred embodiment of the invention, the inhibitor-containing liquid phase is introduced in finely disperse form into the reactor interior containing the gas phase in such a quantity that all the inner solid surfaces contacted by the gas phase are wetted with a preferably continuous inhibitor-containing liquid film. In addition, it is preferred to introduce the inhibitor-containing liquid phase into the reactor interior containing the gas phase without the formation of significant shaded spaces, in other words to ensure that, in reality, the entir einner gas space is also adequately charged with fine liquid droplets. In one embodiment of particular industrial significance, the inhibitor-containing liquid phase is brought into the finely disperse state by spraying.

Accordingly, the new technological statement of the teaching according to the invention presents itself as follows: instead of inhibiting the gas- or vapor-filled interior and the inner wall surfaces in contact therewith with inhibitors introduced in gaseous form, an initially finely disperse liquid phase containing inhibitor is provided in the gas space. The liquid droplets condense on those wall surfaces in contact with the gas phase. The quantity of inhibitor-containing disperse liquid phase introduced in batches or, preferably continuously into the inner gas space is gauged in particular in such a way that a continuous liquid film containing polymerization inhibitor is able to form on the inner wall surfaces. In this way, every possible danger spot for the unwanted initiation of polymerization is protected by inhibitor-containing liquid phase, thus ensuring optimal inhibition of the reaction mixture throughout the entire reaction phase.

In one aprticularly important embodiment, this new principle is put into practice as follows: portions of the liquid reaction mixture containing the polymerization inhibitor are introduced in very finely divided form into the reactor interior, more particularly into the reactor interior filled with gas or vapor phase, either in batches or continuously so that the interior of the reactor is charged with the very finely divided inhibitor-containing liquid phase. The quantity of reaction mixture thus introduced is gauged in such a way that continuous liquid films are formed on the inner walls of the reactor and, in the course of the reaction, flow down these walls into the sump of the reactor so that they recombine with the main quantity of reaction mixture. The advantages of this procedure are clear. Fresh, inhibitor-containing, very finely divided liquid phase is repeatedly introduced into the inner gas space either continuously or in batches. This disperse phase is able to coalesce by droplet agglomeration, but above all by condensation, on the inner walls of the reactor and is thus returned to the reaction mixture. At the same time, the entire inner wall of the reactor is intensively washed with inhibitor-containing liquid phase.

Portions of the reaction mixture can be atomized particularly easily by removing limited quantities of the liquid reaction mixture from the sump of the reactor either in batches or, preferably, continuously and returning them through a spary nozzle to the interior of the reactor filled with gas phase. Technologically, various models are available in this regard. THus, it is possible to use a single spray nozzle or several spray nozzles. The liquid circuit may be provided in the interior of the reactor or in such a way that the portions of liquid phase to be atomized are removed by a pump situated outside the reactor and returned to the interior of the reactor by the spray nozzles. The size of the droplets and the degree of neublization of the liquid phase in the gas-filled interior of the reactor may be influenced to a large extent by the design of the spray nozzles and the way in which they are operated.

If the liquid phase is circulated as described above, it may be advisable to introduce at least a portion of the gas stream containing free oxygen into the partial stream of liquid removed and to return it to the interior of the reactor with that partial stream. It has been found that unwanted blockages of the circulated liquid phase can be avoided in this way. In another important embodiment, the liquid phase is finely dispersed in the interior of the reactor by drawing up portions of the liquid phase into the interior of the reactor and accelerating them in finely dispersed form into the gas-filled interior of the reactor, for example by means of rotating elements which dip into the liquid reaction mixture. A plurality of such rotating elements may also be provided.

In one particularly important embodiment of the invention, the gas phase is withdrawn at least partly from the interior of the reactor and returned to the liquid reaction mixture in such a way that predeterminable portions of the liquid phase are thus entrained by the recycled gas stream and are carried into the gas-filled interior of the reactor. If, where this procedure is adopted, the circulated gas phase is additionally dried, i.e. freed from the water of condensation it has taken up, the esterification reaction can be further intensified and accelerated.

In one particularly preferred embodiment, the reaction mixtures are liquid at room temperature and are at least substantially free from solvents and/or azeotropic entraining agents. In the practical application of this embodiment of the process according to the invention, the water of reaction formed during the esterification reaction is effectively discharged solely by the gas stream introduced into the reaction zone. Depending on the process conditions, air or oxygen-depleted gas mixtures, for example nitrogen/air mixtures, may be used as the gas stream. In general, however, a certain content of free ozygen will be desirable in this gas phase delivered to the reaction mixture. These limited quantities of oxygen activate the inhibitor in known manner during the course of the reaction.

Through the measure according to the invention of distributing the polymerization inhibitor throughout the interior of the reactor by partial atomization of the liquid inhibitor-containing reaction mixture, it is also possible in particular to use the application inhibitor required for the practical application of the reaction products as the reaction inhibitor for the esterification reaction itself. The hitherto typical use of comparatively readily volatile inhibitor components for adequate protection of the gas- or vapor-filled interior of the reactor and the corresponding wall surfaces is no longer necessary. The invention thus enables substantially involatile, but highly effective inhibitor systems or suitably selected, substantially involatile individual inhibitors to be effectively used from the beginning of the reaction to the ultimate practical application of the reaction product. The reaction inhibitor used in the production process need no longer be replaced by the application inhibitor required for practical application.

Suitable polymerization inhibitors are both certain selected individual inhibitor compounds and also inhibitor systems containing several components. It is preferred to use compounds of comparatively low volatility, particularly based on monohydric or polyhydric phenols, particularly suitable polyhydric phenol compounds being dihydric phenols of the hydroquinone or hydroquinone derivative type.

According to the invention, particular significance is attirubted to three selected types for the production of high-purity and, in particular, substantially colorless radiation-curable (meth)acrylic acid esters of the described type. The first of these inhibitors is hydroquinone itself, although special conditions are required for its use in the esterification reaction, as described hereinafter. Fewer problems are involved in the use of a sterically hindered hydroquinone namely di-tert.-butyl hydroquinone. A third important class of polymerization inhibitors are sterically hindered phenol compounds of the tocopherol type, among which considerable significance is attributed in particular to α-tocopheol.

The use of di-tert.-butyl hydroquinone leads readily to light-colored, storable (meth)acrylic acid esters of the desired type. The use of tocopherols, particularly mixtures at least partly containing α-tocopherol, also leads comparatively easily to light-colored poly(meth-)acrylic acid esters of the desired type. If, in their case, slight discoloration of the reaction product should occur during production, particularly in the absence of solvents, under drastic esterification conditions, it may readily be eliminated by aftertreatment, for example with aluminum oxide.

Comparatively more seriour color problems arise in the solventless esterification reaction according to the invention where hydroquinone is used as the polymerization inhibitor. In this case, comparatively serious discoloration of the esterification product does occur in the absence of axuiliary measures and cannot readily be removed by after-treatment of the reaction product. In one particular embodiment, the invention proposes eliminating this problem by simultaneously adding active carbon to the reaction mixture where hydroquinone is used as the polymerization inhibitor. It has surprisingly been found that the combined use of hydroquinone and active carbon suppresses undesirably seriour discoloration of the reaction product, even under drastic esterification conditions; on the other hand, the inhibitor effect of the hydroquinone is not significanlty affected by the presence of active carbon. On completion of the esterification reaction, the reaction mixture merely has to be clarified, for example by filtration, to obtain substqntially colorless reaction product. The inhibitors are typically added to the reaction mixture in quantities of from 200 to 10,000 ppm and preferably in quantities of from about 300 to 2,000 ppm, based in each case on the weight of the reaction mixture consisting of (meth)acrylic acid and polyhydric alcohols.

Where hydroquinone is used in combination with active carbon as the inhibitor system, the quantity of active carbon does not significantly exceed the quantity of hydroquinone in the preferred embodiment. The active carbon is best used in at least about 10 times the quantity by weight of the hydroquinone and preferably in 10 to 100 times and, more preferably, about 20 to 60 times the quantity by weight of the hydroquinone.

Particularls of working with the preferred inhibitors mentioned herein can be found in parallel applications . . . (D 8492, D8493, D 8494 "Processes for the improved production of (meth)acrylic acid esters of polyhydric alcohols (I –III)"), of which the contents are hereby included in the disclosure of the present invention.

Suitable polyalcohols for esterification are, for example, ethylene glycol, propylene glycol, butane-1,4-diol, hexane1,6-diol, neopentyl glycol, diethylene glycol, triethylene glycol, dimethylol propane, glycerol, trimethylol propane, trimethylol hexane, trimethylol ethane, hexane-1,3,5-triol and pentaerythritol. According to the invention, however, particularly suitable polyhydric alcohols are also the alkoxylation products of the above-mentioned polyhydric alcohols, particular signifance being attributed in this regard to the ethoxylation products and/or propoxylation products. Chain-extended polyhydric alcohols of this type may contain considerable quantities of polyalkoxide groups, for example 1 to 50 mol and preferably about 1 to 20 mol ethylene oxide per g-equivalent hydroxyl grups.

Suitable esterification catalysts for the process according to the invention are commerically available organic or inorganic acids or even acidic ion exchangers, particular significance being attributed to the corresponding compounds frequently used in practice, namely p-toluene sulfonic acid and sulfuric acid. The esterifcation catalyst is used in quantities of, for example, from 0.1 to 5% by weight, based on the esterification mixture.

The reactants may be reacted in the absence of solvents or diluents under comparatively drastic conditions. Sump temperatures of at least about 90° C. and, preferably, of at least about 100° C. are preferred for the esterification reaction, the temperature range up to about 150° C. being particularly suitable. The reaction may be carried out under normal pressure, although it is best carried out under reduced pressure. Where the reaction is carried out under reduced pressure, it is possible in one particular embodiment to vary the pressure towards lower pressures either in steps or continuously.

Through the possibility of working under comparatively drastic esterification conditions and, at the same time, reduced pressure, the reaction time is considerably shortened by comparison with hitherto known processes. Thus, yields of at least 90% of the theoretical and, preferably, of at least about 94% of the theoretical may be obtained in the process according to the invention for a reaction time of no more than about 10 hours and, preferably, of no more than about 8 hours at temperature sin the range from about 100° to 140° C. Nevertheless, the reaction products are obtained in the form of a stabilized mass which is light in color or may be effectively purified by a simple aftertreatment.

The crude reaction product containing the acidic esterification cataylst is subsequently subjected to neutralization. This neutralization step may be carried out under known wet conditions, for example by the use of aqueous solutions containing soda and, optionally, sodium chloride. In one preferred embodiment, however, the crude reaction product containing the acidic catalyst is subjected to dry neutralization. Suitable dry neutralizing agents are the oxides and/or hydroxides of the alkali metals, alkaline earth metals, particularly magnesium or calcium, and/or aluminum.

(Meth)acrylic acid and the alcohols may be used in equivalent quantities for the esterification reaction. However, where more than dihydric alcohols are used, it is readily possible only partly to esterify the hydroxyl groups. For full esterification, it may be best to use the acid component in a slight excess over the stoichiometric quantity required for esterification of the hydroxyl grups. This slight excess may amount to at least about 10 mol-%. If desired, an inhibitor may be additionally incorporated in the reaction product on completion of the reaction.

EXAMPLES

Example 1

14.53 kg acrylic acid, 14.18 kg of an ethoxylated trimethylol propane (OH value: 665 mg KOH/g substance), 1.01 kg p-toluene sulfonic acid and 0.047 kg 2,5-di-tert.-butyl hydroquinone (2,000 ppm, based on the quantity of product) were weighed into a 30 liter reactor. Air (100 l/h) was passed through the reaction mixture during the esterification reaction and water was removed. The inhibited reaction mixture was sprayed by means of acompressed-air membrane pump and a one-component nozzle in the upper, non-inhibited interior of the reactor. The product flow rate (40 l/h) was selected so that all parts of the reactor were wetted with inhibited product. To avoid unwanted polymer formation, the inner walls of the pipes were coated with Teflon and air (60 l/h) was additionally introduced into the pressure part of the product circuit. As another measure for inhibiting the condensation part of the reactor, the additionally inhibited distillate was circulated and sprayed in the condenser zone. For a maximum reaction temperature of 105° C. and a vacuum profile of 2 h/400 mbar; 1 h/300 mbar; 0.5 h/200 mbar; 1 h/100 mbar and 0.5 h/23 mbar, the esterification time was 5 hours.

| Crude product: | |
|---|---|
| Acid value: | 17.3 mg KOH/g |
| OH value: | 12.6 mg KOH/g |
| Yield: | 96.9% |
| Gardner color standard number: | <1 |
| Viscosity: | 150 mPa · s |
| H₂O content: | 0.09% |

The crude product was neutralized by addition of 0.53 kg Ca(OH)₂ and stirring for 2 hours at 80° C./50 mbar and was then filtered in a pressure nutsche.

| Product: | |
|---|---|
| Acid value: | <1 mg KOH/g |
| OH value: | 14 mg KOH/g |
| Gardner color standard number: | <1 |

Comparison Example 1

The procedure was as in Example 1, except that there was no spraying of product or distillate during the esterification reaction. Distinct polymer formation was observed both on the cover of the reactor and in the condensation zone after an esterification time of only 30 minutes.

| Crude product: | |
|---|---|
| Acid value: | 39.2 mg KOH/g |
| OH value: | 18 mg KOH/g |
| Yield: | 95.4% |
| Gardner color standard number: | 1 |
| H₂O content: | 0.13% |

The crude product was neutralized by addition of 1.5 kg Ca(OH)₂ and stirring for 2 hours at 80° C./50 mbar and then filtered in a pressure nutsche.

| Product: | |
|---|---|
| Acid value: | <1 mg KOH/g |
| OH value: | 21 mg KOH/g |
| Gardner color standard number: | <1 |
| H₂O content: | 0.17% |

Example 2

12.97 kg acrylic acid, 15.82 kg of a propoxylated neopentyl glycol (OH value: 509 mg KOH/g substance), 1.01 kg p-toluene sulfonic acid and 47 kg 2.5-ditert.-butyl hydroquinone (2,000 ppm, based on the quantity of product) were weighed into a 30 liter reactor. Air (100 l/h) was passed through the reaction mixture during the esterification reaction and water was removed. Part of the inhibited reaction mixture was sprayed by means of a compressed-air membrane pump and a one-component nozzle in the upper, non-inhibited interior of the reactor. The product flow rate (40 l/h) was selected so that all parts of the reactor were wetted with inhibited product. To avoid unwanted polymer formation, the inner walls of the pipes were coated with Teflon and air (60 l/h) was additionally introduced into the pressure part of the product circuit. As another measure for inhibiting the condensation part of the reactor, the additionally inhibited distillate was circulated and sprayed in the condenser zone. For a maximum reaction temperature of 105° C. and a vacuum profile of 2 h/400 mbar; 1 h/300 mbar; 0.5 h/200 mbar; 1 h/100 mbar and 0.5 h/30 mbar, the esterification time was 5 hours.

| Crude product: | |
|---|---|
| Acid value: | 34 mg KOH/g |
| OH value: | 17 mg KOH/g |
| Yield: | 94.4% |
| Gardner color standard number: | <1 |

The crude product was neutralized by addit9ion of 1.3 kg Ca(OH)₂ and stirring for 2 hours at 80° C./50 mbar and was then filtered in a pressure nutsche.

| Product: | |
|---|---|
| Acid value: | <1 mg KOH/g |
| OH value: | 20 mg KOH/g |
| Gardner color standard number: | <1 |

Comparison Example 2

The procedure was as in Example 2, except that there was no spraying of product or distillate during the esterification reaction. Distinct polymer formation was observed both on the cover of the reactor and in the condensation zone after an esterification time of only 40 minutes.

| Crude product: | |
|---|---|
| Acid value: | 20 mg KOH/g |
| OH value: | 20 mg KOH/g |
| Yield: | 95.0% |
| Gardner color standard number: | 1 |

The crude product was neutralized by addition of 0.63 kg Ca(OH)₂ and stirring for 1.5 hours at 80° C./50 mbar and then filtered in a pressure nutsche.

| Product: | |
|---|---|
| Acid value: | <1 mg KOH/g |
| OH Value: | 23 mg KOH/g |
| Gardner color standard number: | <1 |

Example 3

14.53 kg acrylic acid, 14.18 kg of an ethoxylated trimethylol propane (OH value: 665 mg KOH/g substance) and 1.01 kg p-toluene sulfonic acid were weighed into a 30 liter reactor and inhibited w2ith 52.6 kg α-tocopherol (HENKEL KG or A, Duesseldorf, Germany; 2,000 ppm, based on teh quantity of product). Air (100 l/h) was passed through the reaction mixture during the esterification reaction and water was removed. Part of the inhibited reaction mixture was sprayed by means of a compressed-air membrane pup and a one-component nozzle in the upper, non-inhibited interior of the reactor. The product flow rate (40 l/h) was selected so that all parts of the reactor were wetted with inhibited product. To avoid unwanted polymer formation, the inner walls of the pipes were coated with Teflon and air (60 l/h) was additionally introduced into the pressure part of the product circuit. As another measure for inhibiting the condensation part of the reactor, the additionally inhibited distillate was circulated and sprayed in the condenser zone. For a maximum reaction temperature of 105° C. and a vacuum profile of 2 h/400 mbar; 1 h/300 mbar; 0.5 h/200 mbar; 1 h/100 mbar and 0.5 h/25 mbar, the esterification time was 5 hours.

| Crude product: | |
| --- | --- |
| Acid value: | 17.0 mg KOH/g |
| OH value: | 33.6 mg KOH/g |
| Yield: | 91.4% |
| Gardner color standard number: | 7-8 |
| $H_2O$ content: | 0.16% |

The crude product was neutralized by addition of 0.52 kg $Ca(OH)_2$ and stirring for 1.5 hours at 80° C./50 mbar and was then filtered in a pressure nutsche.

| Product: | |
| --- | --- |
| Acid value: | <1 mg KOH/g |
| OH value: | 43 mg KOH/g |
| Gardner color standard number: | 5-6 |
| $H_2O$ content: | 0.42% |

For decolorization, the neutralized and filtered product was stirred for 2 hours at 80° C. with 2.5 kg basic $Al_2O_3$ and then filtered in a pressure nutsche.

| Product: | |
| --- | --- |
| Acid value: | <1 mg KOH/g |
| OH value: | 42 mg KOH/g |
| Gardner color standard number: | <1 |
| $H_2O$ content: | 0.08% |

Comparison Example 3

The procedure was as in Example 3, except that there was no spraying of product or distillate during the esterification reaction. Distinct polymer formation was observed both on the cover of the reactor and in the condensation zone after an esterification time of only 30 minutes.

| Crude proiuct: | |
| --- | --- |
| Acid value: | 23 mg KOH/g |
| OH value: | 19 mg KOH/g |
| Yield: | 95.3% |
| Gardner color standard number: | 8 |

The crude product was neutralized by addition of 0.71 kg $Ca(OH)_2$ and stirring for 1 hour at 80° C./50 mbar and then filtered in a pressure nutsche.

| Neutralized product: | |
| --- | --- |
| Acid value: | <1 mg KOH/g |
| OH Value: | 20 mg KOH/g |
| Gardner color standard number: | 6 |

For decolorization, the neutralized and filtered product was stirred for 2 hours at 80° C. with 2.5 kg basic $Al_2O_3$ and then filtered in a pressure nutsche.

| Product: | |
| --- | --- |
| Acid value: | <1 mg KOH/g |
| OH value: | 22 mg KOH/g |
| Gardner color standard number | <1 |

Example 4

12.97 kg acrylic acid, 15.82 kg of a propoxylated neopentyl glycol (OH value: 509 mg KOH/g substance) and 1.01 kg p-toluene sulfonic acid were weighed into a 30 liter reactor and inhibited with 47 g α-tocopherol (HENKEL; 2,000 ppm, based on the quantity of product). Air (40 l/h) was passed through the reaction mixture during the esterification reaction and water was removed. Part of the inhibited reaction mixture was sprayed by means of a compressed-air membrane pump and a one-component nozzle in the upper, non-inhibited inerior of the reactor. The product flow rate (40 l/h) was selected so that all parts of the reactor were wetted with inhibited product. To avoid unwanted polymer formation, the inner walls of the pipes were coated with Teflon and air (60 l/h) was additionally introduced into the pressure part of the product circuit. As another measure for inhibiting the condensation part of the reactor, part of the additionally inhibited distillate was circulated and sprayed in the condenser zone. For a maximum reaction temperature of 105° C. and a vacuum profile of 2 h/400 mbar; 1 h/300 mbar; 0.5 h/200 mbar; 1 h/100 mbar and 0.5 h/25 mbar, the esterification time was 5 hours.

| Crude product: | |
| --- | --- |
| Acid value: | 24 mg KOH/g |
| OH value: | 20 mg KOH/g |
| Yield: | 94.4% |
| Gardner color standard number: | 7-8 |

The crude product was neutralized by addition of 0.72 kg $Ca(OH)_2$ and stirring for 1 hour at 80° C./50 mbar and was then filtered in a pressure nutsche.

| Neutralized product: | |
| --- | --- |
| Acid value: | <1 mg KOH/g |
| OH value: | 22 mg KOH/g |
| Gardner color standard number: | 6 |

For decolorization, the neutralized and filtered product was stirred for 2 hours at 80° C. with 2.5 kg basic $Al_2O_3$ and then filtered in a pressure nutshce.

| Product: | |
| --- | --- |
| Acid value: | <1 mg KOH/g |
| OH value: | 24 mg KOH/g |
| Gardner color standard number: | <1 |

Comparison Example 4

The procedure was as in Example 4, except that there was no spraying of product or distillate during the esterification reaction. Distinct polymer formation was observed both on the cover of the reactor and in the condensation zone after an esterification time of only 30 minutes.

| Crude product: | |
|---|---|
| Acid value: | 35.1 mg KOH/g |
| OH value: | 25.2 mg KOH/g |
| Yield: | 92.6% |
| Gardner color standard number: | 7-8 |

The crude product was neutralized by addition of 1.09 kg Ca(OH)₂ and stirring for 1 hour at 80° C./5 mbar and then filtered in a pressure nutsche.

| Neutralized product: | |
|---|---|
| Acid value: | <1 mg KOH/g |
| OH value: | 28 mg KOH/g |
| Gardner color standard number: | 5 |

For decolorization, the neutralized and filtered product was stirred for 2 hours at 80° C. with 2.5 kg basic Al₂O₃ and then filtered in a pressure nutsche.

| Product: | |
|---|---|
| Acid value: | <1 mg KOH/g |
| OH value: | 28 mg KOH/g |
| Gardner color standard number: | <1 |

Example 5

1559.5 g acrylic acid, 1521.0 g of an ethoxylated trimethylol propane (OH value 665 mg KOH/g substance), 107.8 g p-toluene sulfonic acid and 124.4 g (5% by weight, based on acrylic acid + polyol) active carbon were weighed into a stirrer-equipped 3 liter reactor and inhibited with 2.5 g hydroquinone (1,100 ppm, based on the quantity of product). Air (40 l/h) was passed through the reaction mixture during the esterification reaction and water was removed. At a stirrer speed of 500 r.p.m., the entire cover region of teh reactor was wetted with inhibited product mixture so that there was no unwanted polymer formation. For a maximum reaction temperature of 105° C. and a vacuum profile of 2 h/400 mbar; 1 h/300 mbar; 1 h/150 mbar; 1 h/40 mbar, the esterification time was 5 hours. The mixture was cooled to 80° C. and filtered in a pressure nutsche.

| Crude product: | |
|---|---|
| Acid value: | 24.8 mg KOH/g |
| OH value: | 23.8 mg KOH/g |
| Yield: | 94.1% |
| Gardner color standard number | <1 |

The crude product was neutralized by addition of 82 g Ca(OH)₂ and stirring for 1 hour at 80° C./50 mbar and then filtered in a pressure nutsche.

| Product: | |
|---|---|
| Acid value: | <1 mg KOH/g |
| OH value: | 29 mg KOH/g |
| Gardner color standard number: | <1 |

Comparison Example 5

The procedure was as in Example 5, except that the stirrer speed was 150 r.p.m. Since the reactor cover was not wetted with inhibited product, distinct polymer formation was observed on unwetted parts of the reactor.

| Crude product: | |
|---|---|
| Acid value: | 28 mg KOH/g |
| OH value: | 17 mg KOH/g |
| Yield: | 95.8% |
| Gardner color standard number: | 1 |

The crude product was neutralized by addition of 92 g Ca(OH)₂ and stirring for 1 hour at 80° C./50 mbar and then filtered in a pressure nutsche.

| Product: | |
|---|---|
| Acid value: | <1 mg KOH/g |
| OH value: | 23 mg KOH/g |
| Gardner color standard number: | 1 |

Example 6

1559.5 g acrylic acid, 1521.0 g of an ethoxylated trimethylol propane (OH value 665 mg KOH/g substance) and 107.8 g p-toluene sulfonic acid were weighed into a 3 liter reactor and inhibited with 4.96 g 2,5-di-tert.-butyl hydroquinone (2,000 ppm, based on the quantity of product). Air (40 l/h) was passed through the reaction mixture during the esterification reaction and water was removed. At a stirrer speed of 500 r.p.m., the entire cover region of the reactor was wetted with inhibited product mixture so that there was no unwanted polymer formation. For a maximum reaction temperature of 105° C. and a vacuum profile of 2 h/400 mbar; 1 h/300 mbar; 1 h/150 mbar; 1 h/40 mbar, the esterification time was 5 hours.

| Crude product: | |
|---|---|
| Acid value: | 32 mg KOH/g |
| OH value: | 21 mg KOH/g |
| Yield: | 94.8% |
| Gardner color standard number | <1 |

The crude product was neutralized by addition of 105 g Ca(OH)₂ and stirring for 1 hour at 80° C./50 mbar and then filtered in a pressure nutsche.

| Product: | |
|---|---|
| Acid value: | <1 mg KOH/g |
| OH value: | 25 mg KOH/g |
| Gardner color standard number: | <1 |

Comparison Example 6

The procedure was as in Example 6, except that, for a stirrer speed of 150 r.p.m., the reactor cover was not wetted with inhibited product. Distinct polymer formation was observed on the unwetted parts of the reactor.

| Crude product: | |
| --- | --- |
| Acid value: | 15 mg KOH/g |
| OH value: | 14 mg KOH/g |
| Yield: | 96.5% |
| Gardner color standard number: | <1 |

The crude product was neutralized by addition of 46 g Ca(OH)₂ and stirring for 1 hour at 80° C./50 mbar and then filtered in a pressure nutsche.

| Product: | |
| --- | --- |
| Acid value: | <1 mg KOH/g |
| OH value: | 18 mg KOH/g |
| Gardner color standard number: | 1 |

Example 7

1297 g acrylic acid, 1582 g of a propoxylated neopentyl glycol (OH value 509 mg KOH/g substance) and 101 g p-toluene sulfonic acid were weighed into a 3 liter reactor and inhibited with 4.79 g α-tocopherol (HENKEL). Air (40 l/h) was passed through the reaction mixture during the esterification reaction and water was removed. At a stirrer speed of 500 r.p.m., the entire cover region of the reactor was wetted with inhibited product mixture so that there was no unwanted polymer formation. For a maximum reaction temperature of 105° C. and a vacuum profile of 2 h/400 mbar; 1 h/300 mbar; 1 h/150 mbar; 1 h/40 mbar, the esterification time was 5 hours.

| Crude product: | |
| --- | --- |
| Acid value: | 15 mg KOH/g |
| OH value: | 10 mg KOH/g |
| Yield: | 97.0% |
| Gardner color standard number | 7-8 |

The crude product was neutralized by addition of 47 g Ca(OH)₂ and stirring for 1 hour at 80° C./50 mbar and then filtered in a pressure nutsche.

| Neutralized product: | |
| --- | --- |
| Acid value: | <1 mg KOH/g |
| OH value: | 12 mg KOH/g |
| Gardner color standard number: | 6 |

For decolorization, the neutralized and filtered product was stirred at 80° C. with 240 g basic Al₂O₃ and then filtered in a pressure nutsche.

| Product: | |
| --- | --- |
| Acid value: | <1 mg KOH/g |
| OH value: | 12 mg KOH/g |
| Gardner color standard number: | 1 |

Comparison Example 7

The procedure was as in Example 7, except that for a stirrer speed of 150 r.p.m., the reactor cover was not wetted with inhibited product. Distinct polymer formation was observed on the unwetted parts of the reactor.

| Crude product: | |
| --- | --- |
| Acid value: | 25 mg KOH/g |
| OH value: | 25 mg KOH/g |
| Yield: | 92.6% |
| Gardner color standard number: | 7-8 |

The crude product was neutralized by addition of 79 g Ca(OH)₂ and stirring for 1.5 hours at 80° C./50 mbar and then filtered in a pressure nutsche.

| Neutralized product: | |
| --- | --- |
| Acid value: | <1 mg KOH/g |
| OH value | 30 mg KOH/g |
| Gardner color standard number: | 5 |

For decolorization, the neutralized and filtered product was stirred at 80° C., with 240 g basic Al₂O₃ and then filtered in a pressure nutsche.

| Product: | |
| --- | --- |
| Acid value: | <1 mg KOH/g |
| OH value: | 29 mg KOH/g |
| Gardner color standard number: | <1 |

We claim:

1. In a process for the preparation of (meth) acrylic acid esters of polyhydric alcohols or alkoxylation derivatives thereof by reaction of (meth) acrylic acid and a polyhydric alochol or its alkoxylation derivative in a reaction zone in the presence of an acidic esterification catalyst and a polymerization inhibitor, the improvement wherein
   A. the reaction zone is purged with an oxygen-containing gas stream, and
   B. one section of the reaction zone is filled with a gas phase into which is charged finely divided liquid droplets containing a polymerization inhibitor.

2. The process of claim 1 wherein the inhibitor-containing finely divided liquid droplets are introduced into the section of the reaction zone containing teh gas phase in such a quantity that all inner solid surfaces defining the reaction zone and contacted by the gas phase are wetted with an inhibitor-containing liquid film.

3. The process of claim 2 wherein the liquid droplets are introduced into the gas phase in such manner that all of said inner solid surfaces are continuously wetted with said liquid film.

4. The process of claim 2 wherein the liquid film flows down the inner solid surfaces coated therewith and is recombined with the reaction mixture.

5. The process of claim 1 wherein the reaction mixture is liquid at room temperature and is at least substantially free from solvents and azeotropic entraining agents.

6. The process of claim 1 wherein the reactin product contains the reaction inhibitor used in the process.

7. The process of claim 1 wherein the polymerization inhibitor is a sterically hindered phenol compound or a sterically unhindered phenol compound.

8. The process of claim 7 wherein the polymerization inhibitor is a tocopherol.

9. The process of claim 7 wherein the polymerization inhibitor is α-tocopherol and/or di-tert. butyl hydroquinone.

10. The process of claim 1 wherein the process is carried out at a temperature in the range of from about 90° to about 150° C. and at subatmospheric pressure.

11. The process of claim 10 wherein the reaction temperature is in the range of from about 100° to about 150° C.

12. The process of claim 1 wherein the reaction zone is purged with air or with mixture of nitrogen and air.

13. The process of claim 1 wherein the polymerization inhibitor is used in a quantity of from about 200 to about 10,000 ppm, based on the weight of the reaction mixture.

14. The process of claim 13 wherein said quantity is from about 300 to about 2,000 ppm.

15. The process of claim 1 wherein the reaction is carried out for a period of time sufficient to result in a yield of product of at least about 90%, said period of time not to exceed 10 hours.

16. The process of claim 1 wherein crude reactino product obtained therefrom is subjected to dry neutralization with an oxide and/or hydroxide of an alkaline earth metal and/or aluminum.

17. The process of claim 1 wherein the reaction product is treated with a decolorizing agent.

18. The process of claim 1 wherein the inhibitor-containing finely divided liquid droplets are introduced into the section of the reaction zone containing the gas phase in such a quantity that all inner solid surfaces defining the reaction zone and contacted by the gas phase are wetted with an inhibitor-containing liquid film and the liquid film flows down the inner solid surfaces coated therewith and is recombined with the reaction mixture; the reaction mixture is liquid at room temperature and is at least substantially free from solvents and azeotropic entraining agents; and the process is carried out at a temperature in the range of from about 90° to about 150° C.

19. The process of claim 1 wherein the reaction temperature is in the range of from about 100° to about 150° C.

20. The process of claim 1 wherein the reaction zone is purged with air or with mixtures of nitrogen and air; and the polymerization inhibitor is a sterically hindered phenol compound and is present in a quantity of from about 200 to about 10,000 ppm, based on the weight of the reaction mixture.

21. The process of claim 20 wherein the sterically hindered phenol compound is present in a quantity of from about 300 to about 2,000 ppm.

22. The process of claim 20 wherein the reaction temperature is in the range of from about 100° to about 150° C.; the reaction is carried out for a period of time sufficient to result in a yeild of product of at least about 90%, said period of time not to exceed 10 hours; the reaction is carried out at subatmospheric pressure; and the crude reaction produt is subjected to dry neutralization.

23. The process of claim 1 wherein the polyhydric alcohols or alkoxylation derivatives thereof as the alcohol moiety of the esters are dihydric to tetrahydric aliphatic saturated alcohols or their alkoxylation derivatives.

24. The process of claim 1 wherein the esters of polyhydric alcohols or alkoyxlation derivatives thereof are esters of at least oen of ethylene glyocl, propylene glyocl, butane-1,4-diol, hexane-1,6-diol, neopentyl glyocl, diethylene glycol, triethylene glycol, dimethylol propane, glycerol, trimethylol propane, trimethylol hexane, trimethylol ethane, hexane-1,3,5-triol, pentaerythritol, and an ethoxylation and/or propoxylation product of any of the foregoing.

25. The process of claim 1 wherein the esters of polyhydric alcohols or alkoyxlation derivatives thereof are esters of at least oen of ethylene glyocl, propylene glyocl, butane-1,4-diol, hexane-1,6-diol, neopentyl glyocl, diethylene glycol, triethylene glycol, dimethylol propane, glycerol, trimethylol propane, trimethylol hexane, trimethylol ethane, hexane-1,3,5-triol, pentaerythritol, and an ethoxylation and/or propoxylation product of any of the foregoing, and wherein the polymerization inhibitor is hydroquinone, a sterically hindered hydroquinone, a sterically hindered phenol compound, or a sterically unhindered phenol compound.

26. The process of claim 25 wherein the polymerization inhibitor is hydroquinone, α-tocopherol, or di-tert.butyl hydroquinone.

* * * * *